US007684032B1

(12) United States Patent
Meeks (10) Patent No.: US 7,684,032 B1
(45) Date of Patent: Mar. 23, 2010

(54) MULTI-WAVELENGTH SYSTEM AND METHOD FOR DETECTING EPITAXIAL LAYER DEFECTS

(75) Inventor: Steven W. Meeks, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 702 days.

(21) Appl. No.: 11/031,248

(22) Filed: Jan. 6, 2005

(51) Int. Cl.
*G01N 21/00* (2006.01)

(52) U.S. Cl. .................................... 356/237.2

(58) Field of Classification Search .............. 356/237.1, 356/237.2–237.5
See application file for complete search history.

(56) References Cited

U.S. PATENT DOCUMENTS

| 3,885,875 | A |   | 5/1975  | Rosenfeld et al. |           |
|-----------|---|---|---------|------------------|-----------|
| 4,182,259 | A |   | 1/1980  | Garner et al.    |           |
| 4,332,477 | A |   | 6/1982  | Sato             |           |
| 4,585,348 | A |   | 4/1986  | Chastang et al.  |           |
| 4,668,860 | A |   | 5/1987  | Anthon           |           |
| 4,870,631 | A |   | 9/1989  | Stoddard         |           |
| 4,873,430 | A |   | 10/1989 | Juliana et al.   |           |
| 4,966,457 | A | * | 10/1990 | Hayano et al.    | 356/239.7 |
| 5,017,012 | A |   | 5/1991  | Merritt, Jr. et al. |        |
| 5,129,724 | A |   | 7/1992  | Brophy et al.    |           |
| 5,189,481 | A |   | 2/1993  | Jann et al.      |           |
| 5,196,906 | A |   | 3/1993  | Stover et al.    |           |
| 5,270,794 | A |   | 12/1993 | Tsuji et al.     |           |
| 5,293,216 | A |   | 3/1994  | Moslehi          |           |
| 5,313,542 | A |   | 5/1994  | Castonguay       |           |
| 5,406,082 | A |   | 4/1995  | Pearson et al.   |           |
| 5,416,594 | A |   | 5/1995  | Gross et al.     |           |
| 5,446,549 | A |   | 8/1995  | Mazumder et al.  |           |
| 5,463,897 | A |   | 11/1995 | Prater et al.    |           |

(Continued)

FOREIGN PATENT DOCUMENTS

JP          3-221804        9/1991

(Continued)

OTHER PUBLICATIONS

W.C. Leung, W. Crooks, H. Rosen and T. Strand, *An Optical Method Using a Laser and an Integrating Sphere Combination for Characterizing the Thickness Profile of Magnetic Media*, Sep. 1989, IEEE Transaction on Magnetics, vol. 25, No. 5. pp. 3659-3661.

(Continued)

*Primary Examiner*—Gregory J Toatley, Jr.
*Assistant Examiner*—Rebecca C Slomski
(74) *Attorney, Agent, or Firm*—Leudeka, Neely & Graham, P.C.

(57) ABSTRACT

The disclosed system provides a method and apparatus for automated detection of a variety of defects within an epitaxial layer by way of an optical surface analysis device containing at least two wavelengths of incident light. A unique defect detection algorithm is provided for generating defect maps for each wavelength of incident light and merging each defect map into one overall defect map in order to detect all defects within an epitaxial layer. The present system is enabled for detecting defects within an epitaxial layer independent of the thickness of the epitaxial layer. Topography, scatter, and phase measurements can also be made in order to increase the accuracy of defect detection.

24 Claims, 8 Drawing Sheets

U.S. PATENT DOCUMENTS

| | | | |
|---|---|---|---|
| 5,586,101 | A | 12/1996 | Gage et al. |
| 5,608,527 | A | 3/1997 | Valliant et al. |
| 5,610,897 | A | 3/1997 | Yamamoto et al. |
| 5,631,171 | A | 5/1997 | Sandstrom et al. |
| 5,633,747 | A | 5/1997 | Nikoonahad |
| 5,644,562 | A | 7/1997 | de Groot |
| 5,694,214 | A | 12/1997 | Watanabe et al. |
| 5,715,058 | A | 2/1998 | Bohnert et al. |
| 5,726,455 | A | 3/1998 | Vurens |
| 5,748,305 | A | 5/1998 | Shimono et al. |
| 5,754,297 | A | 5/1998 | Nulman |
| 5,777,740 | A | 7/1998 | Lacey et al. |
| 5,798,829 | A | 8/1998 | Vaez-Iravani |
| 5,864,394 | A | 1/1999 | Jordan, III et al. |
| 5,875,029 | A | 2/1999 | Jann et al. |
| 5,880,838 | A | 3/1999 | Marx et al. |
| 5,903,342 | A | 5/1999 | Yatsugake et al. |
| 5,909,276 | A | 6/1999 | Kinney et al. |
| 5,951,891 | A | 9/1999 | Barenboim et al. |
| 5,978,091 | A | 11/1999 | Jann et al. |
| 5,985,680 | A | 11/1999 | Singhal et al. |
| 5,986,761 | A | 11/1999 | Crawforth et al. |
| 5,986,763 | A | 11/1999 | Inoue |
| 5,995,226 | A | 11/1999 | Abe et al. |
| 6,028,671 | A | 2/2000 | Svetkoff et al. |
| 6,034,378 | A | 3/2000 | Shiraishi |
| 6,043,502 | A | 3/2000 | Ahn |
| 6,081,325 | A | 6/2000 | Leslie et al. |
| 6,088,092 | A | 7/2000 | Chen et al. |
| 6,091,493 | A | 7/2000 | Stover et al. |
| 6,107,637 | A | 8/2000 | Watanabe et al. |
| 6,118,525 | A | 9/2000 | Fossey et al. |
| 6,134,011 | A | 10/2000 | Klein et al. |
| 6,157,444 | A | 12/2000 | Tomita et al. |
| 6,169,601 | B1 | 1/2001 | Eremin et al. |
| 6,172,752 | B1 | 1/2001 | Haruna et al. |
| 6,201,601 | B1 | 3/2001 | Vaez-Iravani et al. |
| 6,248,988 | B1 | 6/2001 | Krantz |
| 6,271,916 | B1 | 8/2001 | Marxer et al. |
| 6,307,627 | B1 | 10/2001 | Vurens |
| 6,353,222 | B1 | 3/2002 | Dotan |
| 6,384,910 | B2 | 5/2002 | Vaez-Iravani et al. |
| 6,509,966 | B2 | 1/2003 | Ishiguro et al. |
| 6,515,745 | B2 | 2/2003 | Vurens et al. |
| 6,542,248 | B1 | 4/2003 | Schwarz |
| 6,603,542 | B1 | 8/2003 | Chase et al. |
| 6,630,996 | B2 | 10/2003 | Rao et al. |
| 6,639,662 | B2 | 10/2003 | Vaez-Iravani et al. |
| 6,757,056 | B1 | 6/2004 | Meeks et al. |
| 6,804,003 | B1 | 10/2004 | Wang et al. |
| 6,809,809 | B2 | 10/2004 | Kinney et al. |
| 6,825,924 | B2 * | 11/2004 | Uda et al. ................. 356/237.5 |
| 6,937,350 | B2 * | 8/2005 | Shirley ....................... 356/630 |
| 7,164,108 | B2 * | 1/2007 | Lofthouse-Zeis et al. 250/201.1 |
| 7,365,834 | B2 * | 4/2008 | Lewis et al. ............... 356/237.2 |
| 2002/0163634 | A1 * | 11/2002 | Meeks et al. .................. 356/73 |
| 2004/0201837 | A1 * | 10/2004 | Lange ...................... 356/237.2 |
| 2008/0221711 | A1 * | 9/2008 | Trainer ........................ 700/54 |

FOREIGN PATENT DOCUMENTS

| | | |
|---|---|---|
| JP | 04-162215 | 5/1992 |
| JP | 10-227764 | 8/1998 |
| JP | 11-173994 | 7/1999 |
| WO | WO 98/52019 | 11/1998 |

OTHER PUBLICATIONS

Steven W. Meeks, Walter E. Weresin, and Hal J. Rosen, *Optical Surface Analysis of the Head-Disk-Interface of Thin Film Disks*, Jan. 1995, Transactions of the ASME, Journal of Tribology, vol. 117, pp. 112-118.

Steven Meeks, Maxtor and Rusmin Kudinar, *The Next Battleground: Head-Disk Interface*, Mar. 1998, Data Storage, Test & Measurement, pp. 29-30, 34 and 38.

*Laser Scanning Surface Profilometer*, [online], Aug. 1970, [retrieved Jan. 29, 2001], pp. 789-790, Retrieved from the Internet: <URL: http://www.delphion.com/tdbs/tdb?&order=70C101758.

Meeks, Steven W.: "A Combined Ellipsometer, Reflectometer, Scatterometer and Kerr Effect Microscope for Thin Film Disk Characterization," Machine Vision Applications in Industrial Inspection VIII, Proceedings of SPIE, vol. 3966, 2000, pp. 385-391, XP001085220.

* cited by examiner

MULTI-WAVELENGTH SYSTEM AND METHOD FOR DETECTING EPITAXIAL LAYER DEFECTS

BACKGROUND OF THE INVENTION

1. Field of the Invention

The present invention generally relates to the field of detecting defects, such as pits, mounds, particles, scratches, stains, crystalline defects, or the like, on epitaxial layers. More specifically, this invention relates to detecting defects on an epitaxial layer by way of a multi-wavelength, optical surface analyzer.

2. Description of Background Art

Coated thin film disks are used in a variety of industries including the semiconductor and the magnetic hard disk industry. An epitaxial growth process may produce a coating on semiconductor wafers. The process consists of growing a layer of a particular composition upon a substrate, which has a similar crystalline structure. Defects can be caused by a thermal or structural mismatch between the epitaxial layer and the substrate material during the growth process. It is important to be able to detect and classify these defects in order to prevent failure of electronic devices which are patterned upon the epitaxial layer and to control the manufacturing process.

Conventional optical surface analysis techniques are available for defect analysis of transparent epitaxial layers; however, significant shortcomings are present. Conventional surface analysis systems operate at a single laser wavelength. Also, some systems use non-laser light (polychromatic) sources for spot thickness measurement only and not a full surface measurement of the defects of an epitaxial layer. These types of systems are used to measure thickness variations only and are not capable of measuring defects. Polychromatic systems are slow and perform only spot measurements on the wafer surface. As a result these systems only examine a small percentage of the wafer surface and would miss the vast majority of small defects.

Single wavelength laser systems are also available; however, they have difficulty detecting all defects on an epitaxial surface since they suffer from nulls in their sensitivity at certain critical points which result from thickness variations in the epitaxial layer. Critical points are common within monochromatic systems due to the presence of interference fringes that appear in the reflectivity images as the thickness of the sample being analyzed changes.

What is needed is an automated method for detecting a variety of defects contained within a grown epitaxial layer independent of the thickness of the epitaxial layer.

SUMMARY OF THE INVENTION

The present invention overcomes the limitations of conventional system by enabling the detection of a variety of defects within a grown epitaxial layer independent of the thickness of the grown epitaxial layer. The current system provides a method and apparatus for automated detection of a variety of defects within an epitaxial layer by way of at least a dual wavelength optical surface analysis device. By using at least two different wavelengths of light, the current system offers increased sensitivity to defects by decreasing the number of "critical points" where the overall sensitivity of a system goes to zero. A defect map for each wavelength of incident light within the system is generated and merged with the wavelength maps for all other incident wavelengths in order to produce an overall defect map that detects all defects within the epitaxial layer.

The optical inspection system and method of the present invention is provided for detection and classification of particles, pits, scratches, or the like on an epitaxially coated surface (i.e. a disk or wafer) in a single scan of the surface. The optical inspection system uses at least a single electromagnetic beam which may or may not be directed into different planes of incidence, such as orthogonally oriented beams, that are directed at the epitaxial surface. In an embodiment a single electromagnetic beam containing one or more wavelengths, in a single plane of incidence is directed at a disk or wafer and the reflected (specular) light beams are separated by their wavelength. The separated specular light intensities are measured by a detector pair. The present method can categorize defects that are smaller than the size of the beam spot on the object surface. The present invention provides a defect detection algorithm to carry out defect analysis of the epitaxial layer.

DETAILED DESCRIPTION OF THE INVENTION

A preferred embodiment of the present invention is now described with reference to the figures where like reference numbers indicate identical or functionally similar elements. Also in the figures, the left most digits of each reference number corresponds to the figure in which the reference number is first used.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

Figure 1:
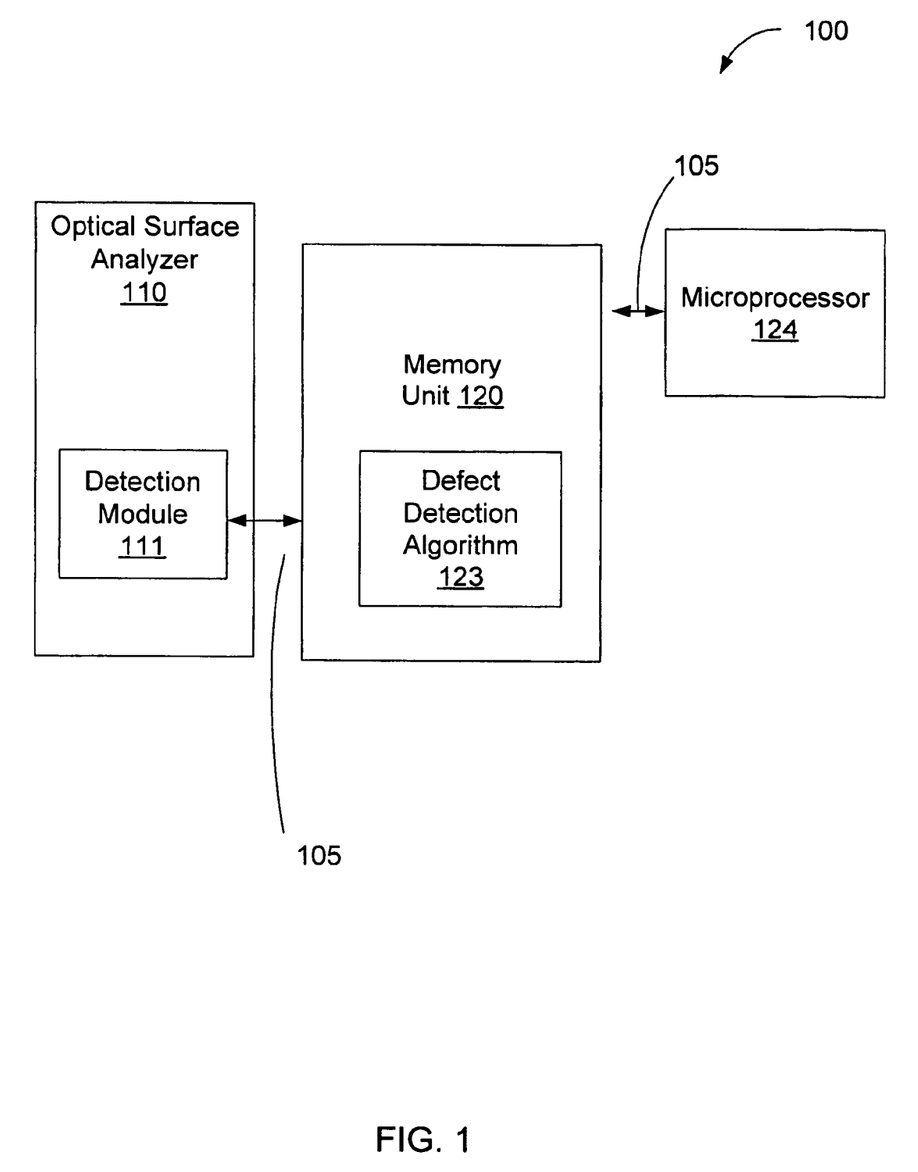
FIG. 1 is a diagram of a dual wavelength optical surface analysis system for measuring defects on an epitaxial layer in accordance with an embodiment of the present invention.

The present invention enables the detection and classification of defects on an epitaxially coated surface by way of a multi-wavelength defect detection system 100 as shown in FIG. 1. The system 100 of the present invention is fully automated and is carried out in a non-invasive manner through the use of an optical surface analyzer (OSA) 110 and a unique defect detection algorithm 123. Detection module 111, within OSA 110, collects topography, specular, scatter, and phase signals from an epitaxially coated surface and these signals are transmitted to memory unit 120 by way of electrical connection 105. The memory unit can be a conventional random access memory (RAM) unit with algorithms stored therein. According to an embodiment, detection module 111 can be a variety of detecting devices, including specular detectors, scatter detectors, surface topography detectors and phase detectors. Within memory unit 120, defect detection algorithm 123 implements a detailed analysis of the processed signals for defect detection and classification. Microprocessor 124 carries out appropriate instructions for optimal defect detection over the entire system 100.

Figure 5A:
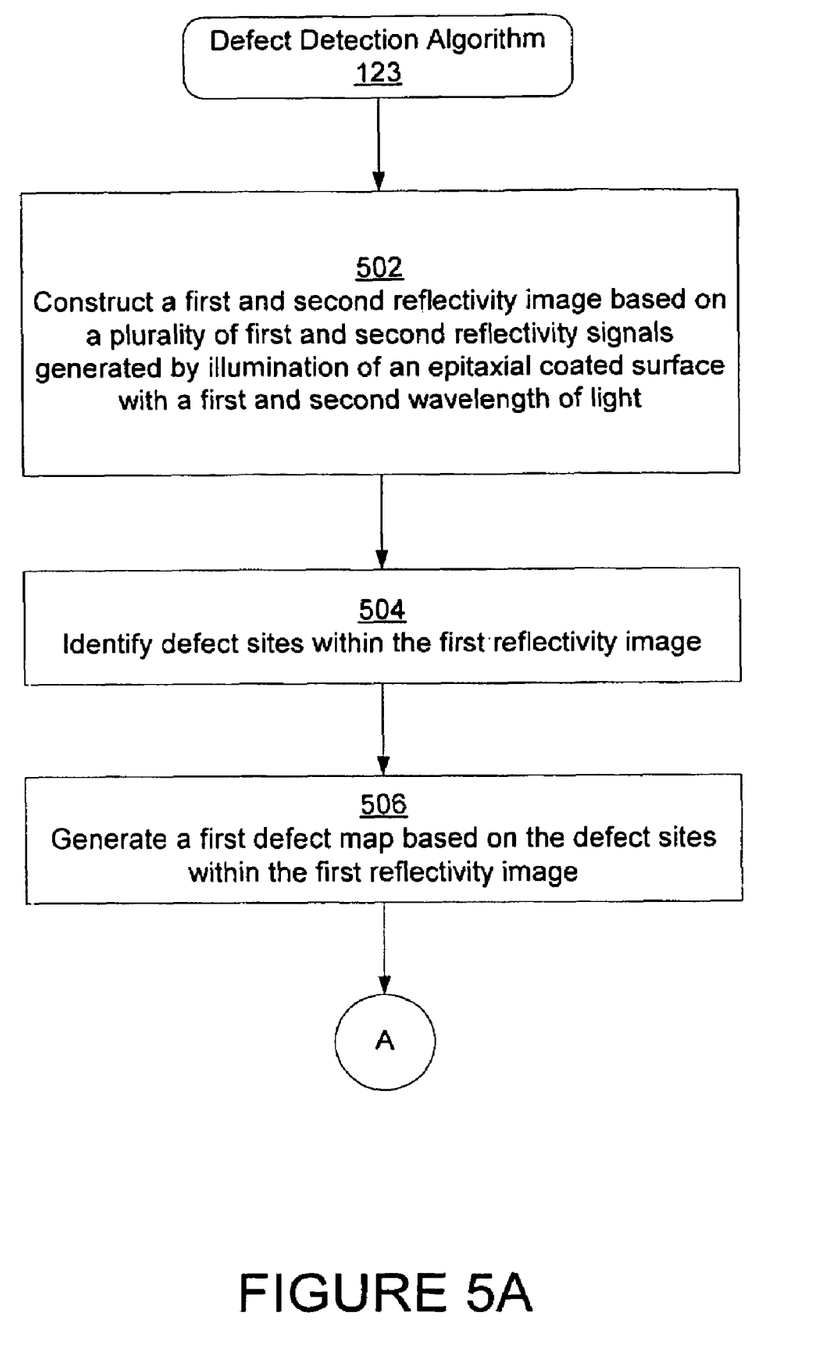
FIGS. 5A-C are a flowchart describing a method for measuring defects on an epitaxial layer in accordance with an embodiment of the present invention.
Figure 5B:
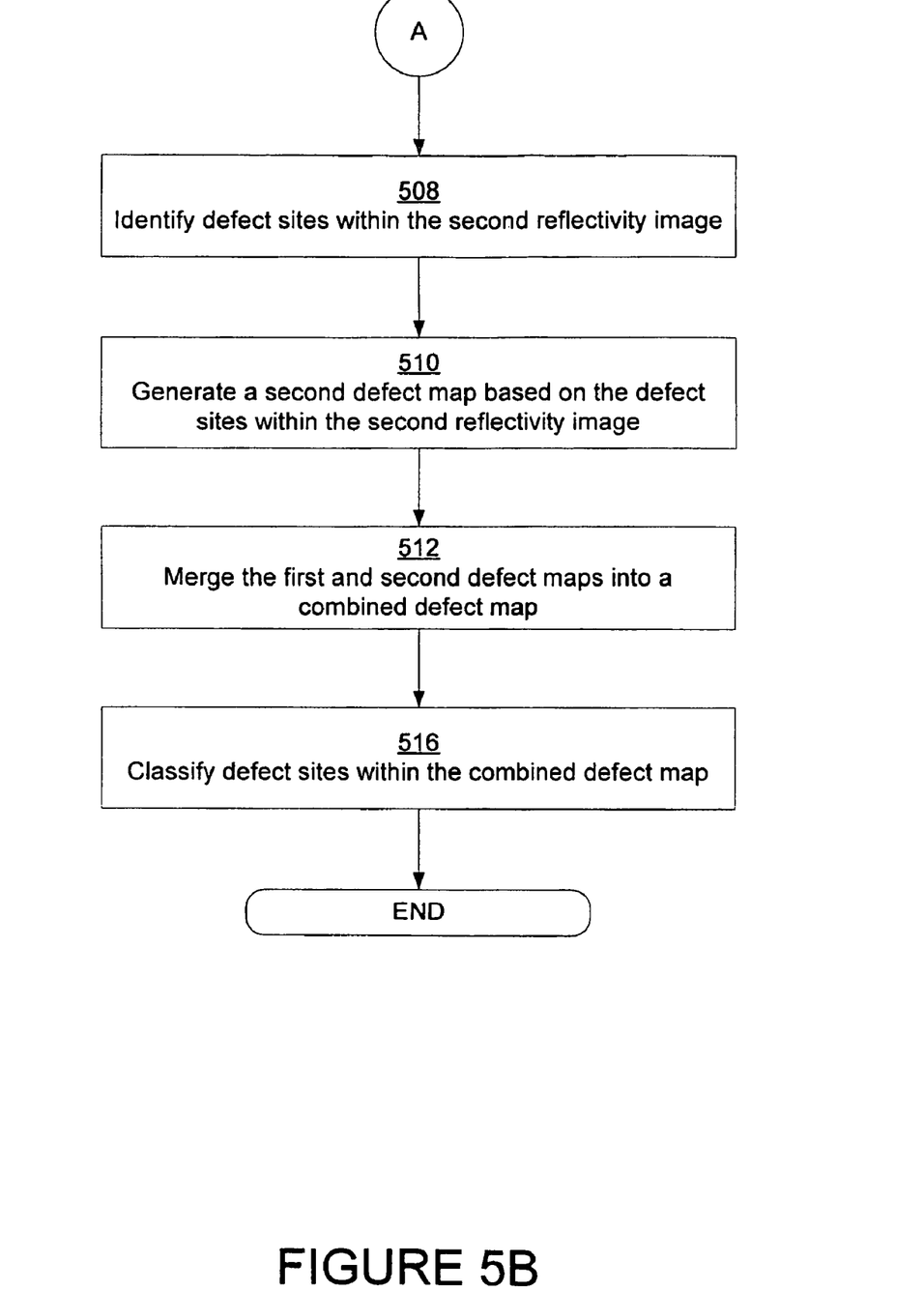
Figure 5C:
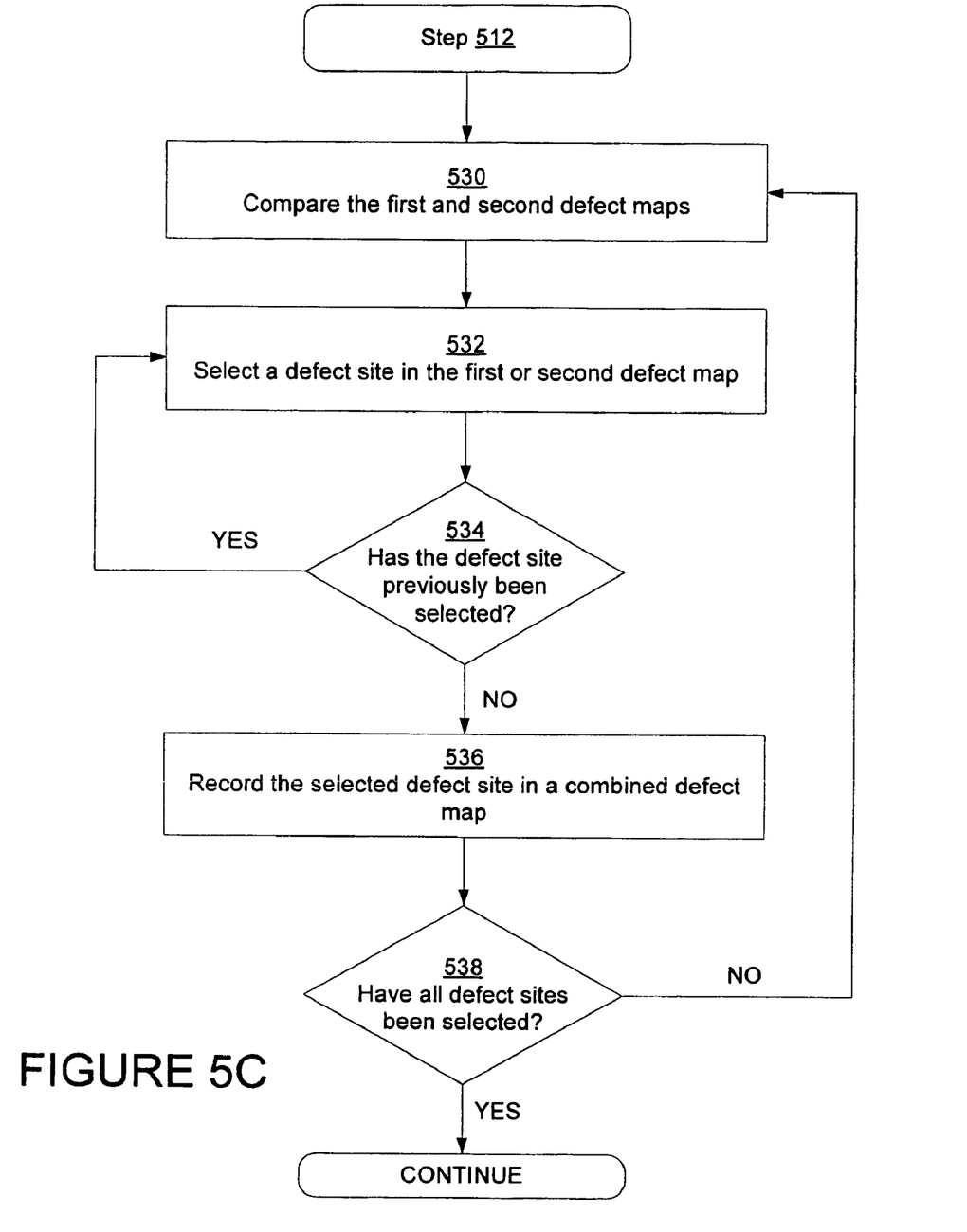

According to an embodiment, as described in FIGS. 5A-C, a reflectivity signal is generated and a reflectivity image is constructed. It is understood that a similar logical implementation as that described in FIG. 5, is available for any particular type of signal, for example, a topography signal, a scatter signal, and a phase signal. The defect detection algorithm 123 constructs 502 a first and second reflectivity image is carried out by an (r, θ) mapping of a portion or the entire epitaxial surface. The mapping can be performed using the optical surface analysis apparatus 100. In an embodiment (FIG. 2), the first and second reflectivity images are constructed 502 based on the generation of at least two reflectivity signals 214 and 212 (or a long wavelength signal and a short wavelength signal) by illumination of an epitaxial coated surface 208 with at least a first and second wavelength of light.

Figure 2:
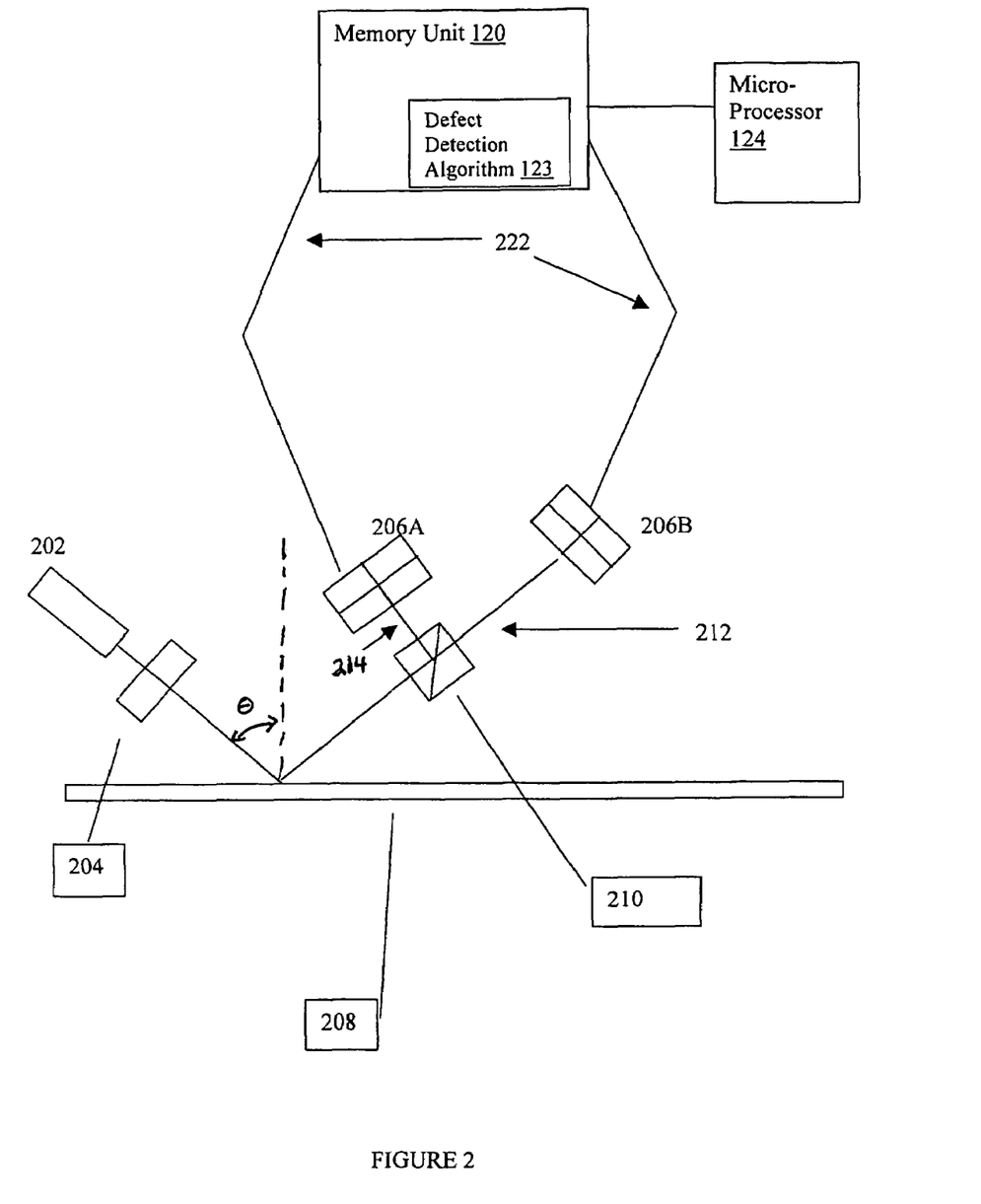
FIG. 2 is a diagram of a dual wavelength optical surface analysis system for measuring defects on an epitaxial layer in accordance with another embodiment of the present invention.

An embodiment of the optical surface analyzer (OSA) 110 is illustrated in FIG. 2 and includes a conventional laser diode 202, available from Rohm Corp. model number RLD2WMUV2 or RLD2WMFZ1 (Rohm Corp. Kyoto, Japan). These lasers can output two wavelengths from a single diode source. This particular model can output both 785 nm (the long wavelength) and 655 nm (the short wavelength). Laser diode 202 emits an electromagnetic signal toward the thin film disk, silicon wafer, photonics wafer, transparent compound semiconductor wafer (such as silicon carbide), other types of semiconductor or transparent wafers (such as sapphire) or a glass substrate. In an embodiment the electromagnetic signal is a light signal having a long wavelength component (e.g. 785 nanometers (nm)) and a short wavelength component (e.g. 655 nm), although a wide variety of wavelengths can be used. Different lasers, each having a discrete wavelength may be combined by the use of a polarizing or non-polarizing beam splitter.

In an embodiment for combining wavelengths with a polarizing beam splitter, one laser is adjusted to S polarization and the other to P polarization. The P polarized laser is placed at the position indicated by laser diode 202 and the S polarized laser is placed orthogonal to it with the polarizing beam splitter between the two lasers. In an embodiment for combining wavelengths with a non-polarizing beam splitter, the lasers are placed in a similar configuration as the polarizing beam splitter arrangement above, but now the polarization of the independent lasers may be adjusted to any polarization which is desired, including elliptically polarized, circularly polarized, S polarized, P polarized, and any linear polarization between P and S. The polarization of the lasers may also be adjusted to be randomly polarized by the addition of a depolarizer available from CVI Laser Optics. By repeating this process with multiple polarizing or non-polarizing beam splitters more than two wavelengths may be combined within a single beam. The angle of incidence of the light signal can be any angle θ between zero and ninety degrees.

In one embodiment (FIG. 2), optical surface analyzer 110 is provided with a conventional zero order half wave plate 204, for rotating polarization, that is commercially available from CVI Laser, Livermore Calif., a conventional short pass dichroic mirror 210 available from CVI Laser Corp. in order to split the electromagnetic signal into a long wavelength signal 214 and a short wavelength signal 212, and a first pair of conventional quadrant detectors 206A and 206B available from Hamamatsu Corp., Hamamatsu City, Japan. Quadrant detector 206A receives the long wavelength signal 214 and quadrant detector 206B receives the short wavelength signal 212. In order to improve the separation of the two wavelengths it may be necessary to add a long pass color filter just before detector 206A and a short pass color filter just before 206B. If it is desired to improve the lateral resolution of the system a focusing lens may be added just after 204 and a collimating lens just before 210.

In one embodiment (not shown), optical surface analyzer 110 is placed upon a mechanical stage that moves the analyzer 110 in the radial direction, while a spindle rotates the coated epitaxial surface 208 in a circumferential direction. The mechanical stage is equipped with a first encoder to record the radial position of the analyzer 110 and the spindle is equipped with a second encoder to record the circumferential position of the coated epitaxial surface 208. In this manner, the epitaxially coated surface 208 may be scanned for defects by way of a (r, θ) mapping of the surface 208.

An alternative embodiment (not shown) for scanning the epitaxially coated surface 208 is to place the optical analyzer 110, or the epitaxially coated surface 208, on an x-y scan stage. The epitaxial coated surface 208, or the optical analyzer 110, is scanned in the x and y directions and in this manner the entire surface may be scanned for defects or topography by way of an (x, y) mapping of the epitaxially coated surface 208. According to an embodiment, the epitaxially coated surface 208 can be constructed from GaN, GaAlAs, or any substantially thin layer (~0.5-10.0 micrometers). In general, according to an embodiment, epitaxially coated surface 208 is deposited on an object or substrate containing a substance like Si, SiC, sapphire, or GaAs. During the growth process of an epitaxial layer on a substrate (like Si), defects are caused by a mismatching of the two materials (i.e. thermal mismatching, structural mismatching, etc.). Other types of defects may be caused by particles, scratches or contamination.

The output reflectivity signals from quadrant detectors 206A and 206B are digitized by a conventional analog to digital converter and directed, by way of electrical conduit 222, to the memory unit 120 of a conventional microprocessor 124. A defect detection algorithm 123, within memory unit 120, analyzes the signals (212, 214) to detect epitaxial layer defects, measure topography, particles, scratches and stains. The logic of the defect detection algorithm, according to one embodiment, is described in FIGS. 5A-C.

Figure 3:
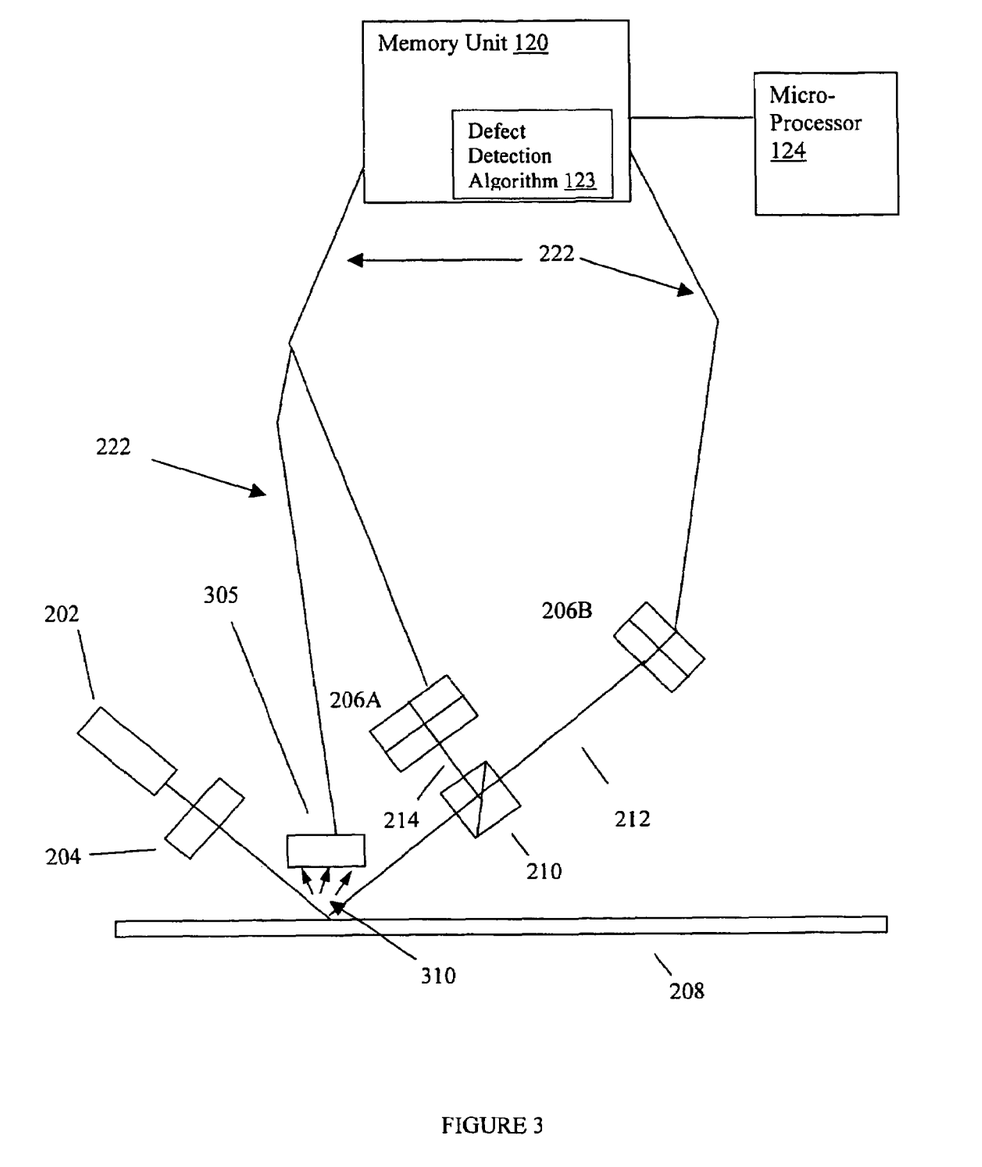
FIG. 3 is a diagram of a dual wavelength optical surface analysis system for measuring defects on an epitaxial layer in accordance with another embodiment of the present invention.

In another embodiment as shown in FIG. 3, an avalanche photodiode, conventional PIN photodiode or photo multiplier (PM) tube 305, for example, detects the scattered component 310 of the signal. Conventional avalanche photodiode 305 is available from Advanced Photonix, Inc., Camarillo, Calif. and may be replaced with a conventional photo multiplier tube (PMT) available from Hamamatsu Corp., Hamamatsu City, Japan. The output scatter signals from PM tube (or photodiode) 305 are digitized by a conventional analog to digital converter and directed, by way of electrical conduit 222, to the memory unit 120 of conventional microprocessor 124. The scatter signals are then analyzed by a defect detection algorithm 123, within memory unit 120, to detect defects, measure topography, particles, and stains. Scattering measurements of this type allow for more accurate detection and classification of defects.

In another embodiment (FIG. 4), the short wavelength signal 212 passes through a zero order quarter wave plate 408 that is used to adjust the phase of the signal 212 so that the beam 212 is split into two parts by a polarization beam splitter that directs the beams into a second pair of quadrant photodetectors 406A and 406B. The short wavelength signal 212 is split by a polarization beam splitter 404 that is rotated by 45° with respect to the plane of incidence, in order to mix the S and P polarized signals (with respect to the original plane of incidence) and to physically separate the beams leading to 406A and 406B. In another embodiment, the polarizing beam splitter may be a Wollaston prism or a Glan Thompson or a Rochon prism beam splitter. The split beams are received by quadrant detectors 406A and 406B. The quadrant detectors are used to compute the phase shift between the split beams, the reflectivity, the optical topographic profiles in the radial and circumferential directions, and the Kerr rotation (if the coating on the surface 208 is magnetic). The phase measurements, carried out according to an embodiment of the present invention, greatly assist in determining the thickness variations of an epitaxial layer and provide valuable information regarding the presence of defects within the layer.

Figure 4:
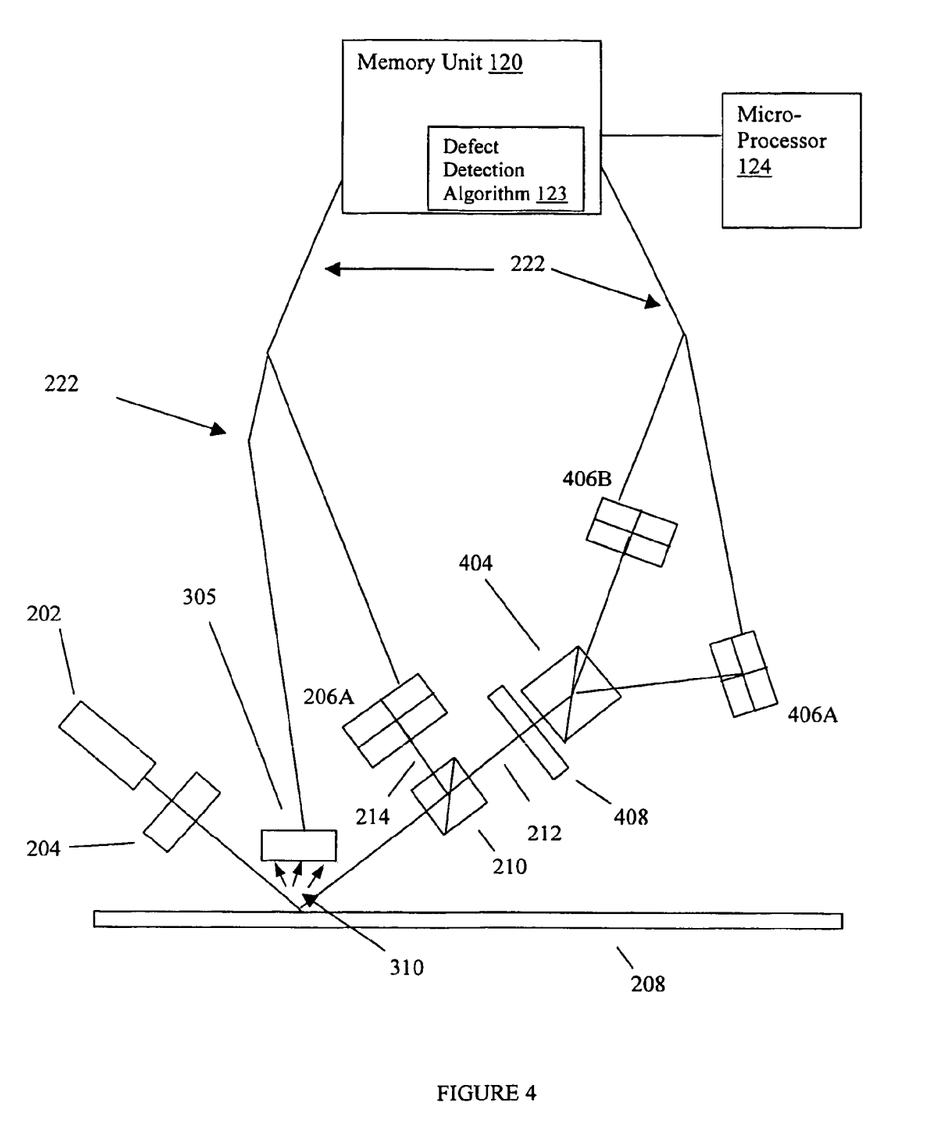
FIG. 4 is a diagram of a dual wavelength optical surface analysis system for measuring defects on an epitaxial layer in accordance with another embodiment of the present invention.

The output signals from quadrant detectors 406A and 406B are digitized by a conventional analog to digital converter and directed, by way of electrical conduit 222, to the memory unit 120 of a conventional microprocessor 124. The defect detection algorithm 123, within memory unit 120, analyzes the signals (212, 214) to detect defects, measure topography, and measure stains. The specular reflectivity of the surface 208 at the short wavelength 212 is obtained by summing the four quadrants of detector 406A and adding the result to the sum of the four quadrants of detector 406B. The specular reflectivity of the surface 208 at the long wavelength 214 is obtained by summing the four quadrants of detector 206A.

In general, output data, within any particular embodiment of the present invention, is detected by a particular detector and digitized simultaneously for all wavelengths of incident light. During the data digitization process, a corresponding digital image is created for each wavelength of incident light. Another embodiment of the present invention enables output data to be detected and digitized sequentially. After the output data is digitized, defect detection algorithm 123 acts on the digital images, either sequentially or simultaneously, to generate defect maps.

Returning to FIGS. 5A-5B, steps 504-510 are carried out by identifying defect sites and generating corresponding defect maps. Images acquired from specular/spatial detectors (quadrant detectors 206A and 206B) and/or scatter detector 305 and/or quadrant photodetectors 406A and 406B are processed through a one-dimensional median filter to flatten each image and remove the global background (long wavelength) variation of the images. The flattening filter also serves as the analysis kernel and is typically set to three to five times the length of the smallest feature to be resolved properly. In this case typical epitaxial defects are about 10 to 300 microns long on the OSA image and hence an analysis kernel of 1000 micrometers can be used. The local background noise is measured at various locations on the image and an appropriate analysis threshold is selected based on the noise level. As the analysis kernel passes through the image, the central data point for each kernel length is compared against the local mean and if the difference exceeds the analysis threshold, the data point is marked for further analysis. Such marked areas are identified 504 as 'defect sites'. After the specular and/or scatter and/or topography images are filtered by the flattening filters and background adjusted by the analysis thresholds, a specular defect map, and/or phase defect map and/or scatter defect map and/or topography defect map are generated 506 based upon illumination of the epitaxial surface with a first wavelength of light. A conglomeration of specular, phase, scatter, or topography defect sites constitute a specular, phase, scatter, or topography defect map. The processed images are used as the primary images for the corresponding defect map when detecting the presence of epitaxial defects.

Steps 508 and 510 are carried out in a similar fashion as steps 504 and 506 to generate a second defect map based upon a second wavelength of illumination.

The defect detection algorithm 123 then merges 512 the defect maps into a combined defect map by, for example, forming the union of the first and second defect maps. A more detailed description of the merging 512 process is set forth in FIG. 5C. With reference to FIG. 5C, the defect detection algorithm 123 compares 530 the first and second defect maps and a defect site found in either the first defect map or the second defect map that is selected 532 for further analysis in the combined defect map. Step 534 verifies that a defect site from either the first defect map or second defect map is counted only once. According to an embodiment of the present invention, a stitching routine (or stitching algorithm), where one or more pixels from the combined defect map are stitched together, insures that only non-contiguous defect sites are recognized by the defect detection algorithm.

When the first and second reflectivity images are generated, intensity variations can exist between the first and second reflectivity signals. In general, the intensity of a reflectivity signal due to light incident upon a defect site is dependent upon the wavelength of light that is incident upon the defect; therefore, in order to insure that no defect sites are selected more than once, the stitching routine pieces together only non-contiguous defect sites. A stitching algorithm is used to piece together detected defect pixels which may be separated from the main body of the defect by one or two pixels. In other words, the detected defect pixels may appear as a main island surrounded by many tiny islands. The human eye and brain tells us that the actual defect consists of the main island plus the tiny islands. The stitching algorithm reaches out from the main island (defect) by one or two pixels and if it encounters another defect, it will add its area to the total size of the defect. In this manner a defect consisting of a main body and many small bodies is stitched into a single defect.

Upon selecting 532 a defect site in the first or second defect map, and verifying 534 that the site has been counted only once, the defect site is recorded 536 in a combined defect map for classification 516. When all defect sites have been selected 538 from either the first or second defect map, the defect detection algorithm 123 returns to step 516 for classification of the defect sites in the combined defect map. Methods for classifying 516 defects, according to an embodiment of the present invention, can be found in U.S. Pat. No. 6,757, 056 which is incorporated by reference herein in its entirety.

Figure 6:
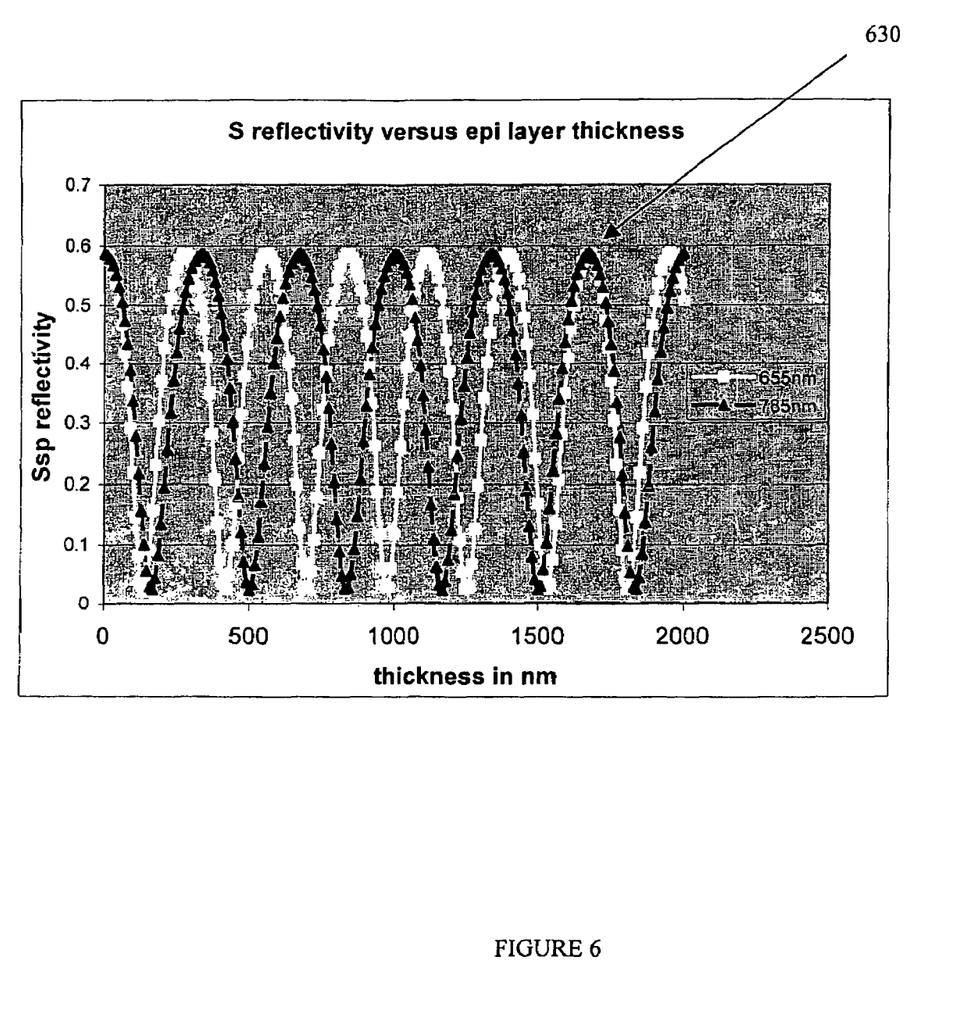
FIG. 6 is a diagram of a typical reflectivity versus thickness of the epitaxial layer generated by a system for measuring defects on an epitaxial layer in accordance with an embodiment of the present invention.

FIG. 6 is a diagram of a typical reflectivity versus epitaxial layer thickness generated by a system for measuring defects on an epitaxial layer in accordance with an embodiment of the present invention. A problem in the detection of defects on epitaxial layers is that the sensitivity to thickness of the epitaxial layer is wavelength dependent. FIG. 6 shows the S specular reflectivity versus thickness for an epitaxial layer deposited on a silicon substrate. The light colored curve is for a laser wavelength of 655 nm and dark colored curve is for laser wavelength of 785 nm. Each of the curves goes through periodic cycles as the thickness of the epitaxial layer changes from 0 to 2000 nm. The maximum thickness sensitivity occurs when the curves have the steepest slope and the zero in sensitivity occurs when the curves have a critical point (zero slope). As a result, when using a single wavelength, defects cannot be detected at the critical points. However, if at least two wavelengths are used over the range from 0 to 2000 nm, only a single thickness, at point 630 where the epitaxial thickness is 1700 nm, occurs where both wavelengths simultaneously have a critical point. Therefore, the instrument of the present invention, which uses at least two wavelengths of incident light, is extremely effective when detecting thickness related defects since it has very few points where its sensitivity goes to zero.

An alternate embodiment for detecting the defects from each wavelength is to perform the detection with an on-the-fly approach. This means that the detection algorithm is performed while the data is streaming into the computer processor. The algorithm detects defects in each wavelength image and records (stores in memory) the amplitude, size and location of each defect. The final result is a merged map which shows the location of each and every defect. The advantage of this approach is that it does not require the storage of a large amount of data. The only data that is stored is the amplitude, size and location of the defects.

While the invention has been particularly shown and described with reference to a preferred embodiment and various alternate embodiments, it will be understood by persons skilled in the relevant art that various changes in form and details can be made therein without departing from the spirit and scope of the invention.

The invention claimed is:

1. A method to detect a defect on or within a surface of a thin layer of material on an object, comprising:
   contemporaneously directing, onto the surface of the object, a radiation beam from a single source having at least a first component at a first wavelength and a second component at a second wavelength, different from the first wavelength;
   generating a first signal set from radiation at the first wavelength reflected from the surface by receiving a portion of the radiation at the first wavelength reflected in a first quadrant detector;
   generating a second signal set from radiation at the second wavelength reflected from the surface by receiving a portion of the radiation at the second wavelength reflected in a second quadrant detector;
   where the first quadrant detector and the second quadrant detector are separate detectors, and the first signal set and the second signal set are contemporaneously generated, and
   identifying the defect on or within the surface of the thin layer of material on said object from the first signal set and the second signal set.

2. The method of claim 1, wherein contemporaneously directing, onto the surface of the object, a radiation beam from a single source having at least a first component at a first wavelength and a second component at a second wavelength, different from the first wavelength comprises:

polarizing the first component to a first polarization state; and polarizing the second component to a second polarization state.

3. The method of claim 1, further comprising:
generating a third signal set from radiation at the first wavelength scattered from the surface; and
generating a fourth signal set from radiation at the second wavelength scattered from the surface.

4. The method of claim 1, further comprising:
splitting the radiation from the first component at the first wavelength reflected from the surface into a first radiation beam and a second radiation beam;
detecting a phase difference between the first radiation beam and the second radiation beam; and
generating a fifth signal set from the phase difference.

5. The method of claim 1, wherein: identifying the defect on or within the surface of the thin layer of material on said object from the first signal and the second signal comprises:
generating a first defect map from the first signal set;
generating a second defect map from the second signal set; and
merging the first defect map and the second defect map to form a combined defect map.

6. The method of claim 5, wherein generating a first defect map from the first signal set comprises:
generating a first reflectivity image;
establishing a background noise reflectivity level on the first reflectivity image;
comparing a reflectivity level for at least one locality on the first reflectivity image with the background noise level; and
marking the at least one locality as a potential defect when a difference between the reflectivity level at the at least one locality and the background noise level exceeds a threshold.

7. The method of claim 6, wherein generating a second defect map from the second signal set comprises:
generating a second reflectivity image;
establishing a background noise reflectivity level on the second reflectivity image;
comparing a reflectivity level for at least one locality on the second reflectivity image with the background noise level; and
marking the at least one locality as a potential defect when a difference between the reflectivity level at the at least one locality and the background noise level exceeds a threshold.

8. The method of claim 5, wherein merging the first defect map and the second defect map comprises:
comparing the first defect map and second defect maps; and
constructing a combined defect map from the data points on the first defect map and the second defect map.

9. A system to detect a defect on or within a surface of a thin layer of material on an object comprising:
a radiation targeting assembly to direct contemporaneously, onto the surface of the object, a radiation beam from a single source having at least first component at a first wavelength and a second component at a second wavelength, different from the first wavelength; and
a first quadrant detector assembly to generate a first signal set from radiation at the first wavelength reflected from the surface;
a second quadrant detect assembly to generate a second signal set from radiation at the second wavelength reflected from the surface;

where the first quadrant detector assembly and the second quadrant detector assembly are separate assemblies, and the first signal set and the second signal set are contemporaneously generated, and a defect detection algorithm to identify the defect on or within the surface of the thin layer of material on said object from the first signal set and the second signal set.

10. The system of claim 9, wherein:
the first detector assembly receives a portion of the radiation at the first wavelength reflected in a first quadrant detector; and
the second detector assembly receives a portion of the radiation at the first wavelength reflected in a second quadrant detector.

11. The system of claim 9, further comprising:
a polarizer to polarize the first component to a first polarization state; and
a polarizer to polarize the second component to a second polarization state.

12. The system of claim 9, further comprising a detector to:
generate a third signal set from radiation at the first wavelength scattered from the surface; and
generate a fourth signal set from radiation at the second wavelength scattered from the surface.

13. The system of claim 9, further comprising:
a beam splitter to split the radiation from the first component at the first wavelength reflected from the surface into a first radiation beam and a second radiation beam;
at least one detector to detect a phase difference between the first radiation beam and the second radiation beam and generate a fifth signal set from the phase difference.

14. The system of claim 9, wherein the defect detection algorithm: identifies the defect on or within the surface of the thin layer of material on said object from the first signal and the second signal comprises:
generates a first defect map from the first signal set;
generates a second defect map from the second signal set; and
merges the first defect map and the second defect map to form a combined defect map.

15. The system of claim 14, wherein the defect detection algorithm:
generates a first reflectivity image;
establishes a background noise reflectivity level on the first reflectivity image;
compares a reflectivity level for at least one locality on the first reflectivity image with the background noise level; and
marks the at least one locality as a potential defect when a difference between the reflectivity level at the at least one locality and the background noise level exceeds a threshold.

16. The system of claim 15, wherein the defect detection algorithm:
generates a second reflectivity image;
establishes a background noise reflectivity level on the second reflectivity image;
compares a reflectivity level for at least one locality on the second reflectivity image with the background noise level; and
marks the at least one locality as a potential defect when a difference between the reflectivity level at the at least one locality and the background noise level exceeds a threshold.

17. The system of claim 14, wherein the defect detection algorithm:
compares the first defect map and second defect maps; and constructs a combined defect map from the data points on the first defect map and the second defect map.

18. The method of claim 1, wherein the first wavelength is 785 nanometers and the second wavelength is 655 nanometers.

19. The system of claim 9, wherein the first wavelength is 785 nanometers and the second wavelength is 655 nanometers.

20. The system of claim 9, further comprising:
a dichroic mirror placed between the object and the detector assemblies;
a long pass color filter placed between the first detector assembly and the dichroic mirror; and
a short pass color filter placed between the second detector assembly and the dichroic mirror.

21. The system of claim 20, further comprising:
a focusing lens placed between the radiation beam source and the object; and
a collimating lens placed between the object and the dichroic mirror.

22. The system of claim 9, wherein:
the first and second detector assemblies are placed on a first mechanical stage which moves the first and second detectors in a first direction; and
the object is placed on a second mechanical stage, different than the first mechanical stage which moves the object in a second direction.

23. The system of claim 22, wherein:
the first direction is a radial direction with respect to the object; and
the second direction is a circumferential direction with respect to the object.

24. The system of claim 22, wherein:
the first direction is an x or y direction with respect to a known point on the object; and
the second direction is perpendicular to the first direction.

* * * * *